United States Patent
Choudhary et al.

(10) Patent No.: US 10,849,953 B1
(45) Date of Patent: Dec. 1, 2020

(54) FOOD SUPPLEMENT TO ALLEVIATE SYMPTOMS OF PARKINSON'S DISEASE

(71) Applicants: Muhammad Iqbal Choudhary, Karachi (PK); Atta-Ur Rahman, Karachi (PK); Atia-Tul Wahab, Karachi (PK); Humaira Zafar, Karachi (PK)

(72) Inventors: Muhammad Iqbal Choudhary, Karachi (PK); Atta-Ur Rahman, Karachi (PK); Atia-Tul Wahab, Karachi (PK); Humaira Zafar, Karachi (PK)

( * ) Notice: Subject to any disclaimer, the term of this patent is extended or adjusted under 35 U.S.C. 154(b) by 0 days.

(21) Appl. No.: 16/447,819

(22) Filed: Jun. 20, 2019

(51) Int. Cl.
| | | |
|---|---|---|
| *A61K 36/8962* | (2006.01) |
| *A61K 36/736* | (2006.01) |
| *A61K 36/48* | (2006.01) |
| *A61K 36/81* | (2006.01) |
| *A61P 25/28* | (2006.01) |
| *A61K 36/61* | (2006.01) |
| *A61K 36/9066* | (2006.01) |
| *A61K 36/82* | (2006.01) |
| *A61K 36/87* | (2006.01) |

(52) U.S. Cl.
CPC .......... *A61K 36/8962* (2013.01); *A61K 36/48* (2013.01); *A61K 36/61* (2013.01); *A61K 36/736* (2013.01); *A61K 36/81* (2013.01); *A61K 36/82* (2013.01); *A61K 36/87* (2013.01); *A61K 36/9066* (2013.01); *A61P 25/28* (2018.01)

(58) Field of Classification Search
None
See application file for complete search history.

(56) References Cited

U.S. PATENT DOCUMENTS

2014/0141082 A1*  5/2014  Gao ........................ A61K 36/45
424/474

* cited by examiner

*Primary Examiner* — Ralph J Gitomer
(74) *Attorney, Agent, or Firm* — Sarfaraz K. Niazi

(57) ABSTRACT

A food supplement to reduce symptoms of Parkinson's disease is disclosed. The food supplements contains a mixture of garlic, almond, peanut, tomato, grape, clove, black eye pea turmeric, tea and velvet bean.

2 Claims, No Drawings

FOOD SUPPLEMENT TO ALLEVIATE SYMPTOMS OF PARKINSON'S DISEASE

BACKGROUND OF THE INVENTION

The worldwide prevalence of Parkinson's disease (hereinafter PD) ranges between 5 to 35 per 0.1 million individuals annually. The disease is rare before the age of 50 years, and the incidence increases 5-10 fold in age groups of 60-90 years. The clinical symptoms of Parkinson's disease include bradykinesia, rigidity, or tremors. The onset of motor symptoms is unilateral throughout the disease. Furthermore, many patients with Parkinson's disease also possess non-motor symptoms, including cognitive impairment, disorders of sleep and mood, autonomic dysfunctions, and disturbance in sensory symptoms. The cardinal motor symptoms of Parkinson's disease are the result of degeneration of dopaminergic neurons in brain (the substantia nigra pars *compacta*) that leads to dopamine depletion.

Due to the complexity of Parkinson's disease, its treatment requires a combination of medical, complementary, and supportive therapies, including exercise, massage, speech therapy, rehabilitation, diet, etc. With the deeper understanding of the mechanisms that regulate the dopaminergic transmission in nigrostriatal regions, various pharmacological targets have been identified for dopaminergic therapies.

Parkinson's disease has no cure, although treatments are available that help to manage the symptoms, and maintain the quality of life. The drugs for the treatment of PD are categorized into three types, including drugs that help to increase the level of dopamine, drugs that affect the level of acetylcholine, and the one that help to control the non-motor symptoms. All these pharmacological treatments have their own limitations, and are associated with adverse effects. For instance, dopamine agonist can execute significant risks for individuals with cardiovascular diseases, depression, or renal insufficiency.

Currently, the treatment of PD patients involves the use of different drugs in combination, based on the tolerance level of individual patients to cope up with the adverse effects of these drugs. Sooner or later the drugs need to be changed as they become ineffective. Majority of the Parkinson's disease patients undergo a gradual decline in their health as the nervous system has already weakened. This health decline ultimately leads to severe disability. Moreover, the medicines and care of these patients are costly, and are required for entire remaining life.

Therefore, there is an urgent need to develop effective, safe, and less-expensive approaches for the management of the PD symptoms. This can be done by using natural sources to manage PD symptoms that will have lesser adverse effects on quality of life. Various medicinal and dietary plants and natural products have been reported to possess anti-Parkinson's effects. Based on this hypothesis, we have developed a new dietary health supplement for the management and/or treatment of Parkinson's disease. Only mineral water was used to mix the ingredients. The resulting formulation can be used in humans as the dietary health supplement, and has no chemical based ingredients. It is, therefore, safe, effective, and non-toxic.

BRIEF SUMMARY OF THE INVENTION

Parkinson's disease is a neurodegenerative disorder that has various layers of complexities. Till date, there is no cure for the disease but the only aim is to manage the motor and non-motor symptoms of PD. Different types of drugs are available to manage the symptoms of PD, including dopamine agonists, non-dopaminergic agents, and catechol-o-methyl-transferase (COMT) inhibitors. However, with the passage of time, the effects of these drugs decrease, followed by adverse effects such as dyskinesia, hallucination, sleepiness, and many others. The current research on neurological diseases, therefore emphasizes on the use of nutritional supplements so that the adverse effects can be minimized, along with improvement in life style of these patients.

Based on these facts, an extensive literature survey was carried out and the dietary plants reported for anti-Parkinson's, antioxidant, and neuroprotective effects were selected. This includes *Allium sativum* L., *Prunus dulcis* (Mill.) D. A. Webb., *Arachis hypogaea* L., *Solanum lycopersicum* L., *Vitis vinifera* L., *Eugenia caryophyllata* Thunb., *Vigna unguiculate* L., *Curcuma longa* L., *Camellia sinensis* L., and *Mucuna puriens* L. The ingredients were mixed using pure mineral water, and no organic solvent was used. The effect of this dietary health supplement was pre-clinically studied in animal model of Parkinson's disease (Male Wistar rats). The supplement was able to significantly improve the PD symptoms in rats. 37.5% Rats at score 8 showed improvement in PD symptoms, and were decreased to scores 4 and 2 (with better mobility, stable postural stability, and white furs except tremors). 100% Rats with score 4 and 6 showed improvements in their PD symptoms, and their scores were lowered to 2. 100% Rats at score 2 showed improvement in various PD symptoms. such as better mobility, stable postural ability, and white furs except tremors that were not treated completely in any rat. The acute toxicity studies of testing health supplement was carried out according to OECD guidelines at 2,000, and 5,000 mg/kg. The supplement did not show any toxic effect during the toxicity studies in animals. The chronic toxicity has also been tested for 3 months, and no adverse effect was seen in the animals.

Open label clinical trials on a small group of PD patients were also conducted under the supervision of experienced neurologists. The health supplement has caused a significant improvement in the symptoms of PD, such as improved speech and clarity in words, and voice, sensory input (Patient can sense before falling down and can hold any object to be stable), relief in muscular pain specially in legs and feet, decreased drowsiness, increased physical activity, and improved body balance (helps patient to walk properly). Therefore, it is concluded that the use of this supplement can help to improve the quality of life in PD patients, and additionally it has no adverse effects whatsoever.

DETAILED DESCRIPTION OF THE INVENTION

The dietary supplement is composed of ten dietary plant materials, mixed in a specific proportion. The components include *Allium sativum* L., *Prunus dulcis* (Mill.) D. A. Webb., *Arachis hypogaea* L., *Solanum lycopersicum* L., *Vitis vinifera* L., *Eugenia caryophyllata* Thunb., *Vigna unguiculate* L., *Curcuma longa* L., *Camellia sinensis* L., and *Mucuna pruriens* L. Only mineral water has been used to mix the ingredients. The detailed description for the selection of above mentioned dietary plants are described below:

The rhizomes of *Allium sativum* L. (garlic) were selected due to its reported anti-PD effect. Fresh garlic cloves/garlic capsules have shown significant effects in PD patients. Dry fruits of *Prunus dulcis* (Mill.) D. A. Webb (almond), and *Arachis hypogaea* L. (peanuts) were selected due to their reported neuroprotective, as well as antioxidant effects. Fruits of *Solanum lycopersicum* L. (tomato) were used due to their reported anti-PD effect. Fruits of *Vitis vinifera* L. (red grapes) are reported for antioxidant effects, and their ability to help in neuronal survival. Oil of *Eugenia caryophyllata* Thunb. (clove) was used as it has been reported for anti-PD effect. Dry seeds of *Vigna unguiculata* L. (black eyed cowpea) was selected due to the presence of 0.45% L-DOPA.

The rhizomes of *Curcuma longa* L. (turmeric) were selected as they reported to protect the dopaminergic neurons against α-synuclein induced neurotoxicity. Leaves of *Camellia sinesis* L. (green tea) were selected as they are widely reported for their neuroprotective, and antioxidant effects. Green tea is also reported to attenuate the dopamine depletion, and increase dopaminergic neuronal survival in MPTP induced PD model. Seeds of *Mucuna puriens* L. (velvet beans) are a rich source of L-DOPA so it was selected for this anti-PD formulation.

Procedure for the Preparation of Dietary Health Supplement

| | |
|---|---|
| i. *Allium sativum* L. | Fresh juice of rhizomes |
| ii. *Prunus dulcis* (Mill.) D.A. Webb. | Dry fruit powder |
| iii. *Arachis hypogaea* L. | Dry fruit powder |
| iv. *Solanum lycopersicum* L. | Fruit dried under shade and then powdered |
| v. *Vitis vinifera* L. | Fresh juice |
| vi. *Eugenia caryophyllata* Thunb. | Seed oil |
| vii. *Vigna unguiculata* L. | Dried seed powder |
| viii. *Curcuma Longa* L. | Rhizome powder |
| ix. *Camellia sinesis* L. | Leaves extract |
| x. *Mucuna purines* L. | Roasted seed powder |

The supplement including *Allium sativum* L., *Prunus dulcis* (Mill) D. A. Webb., *Arachis hypogaea* L., *Solanum lycopersicum* L., *Vitis vinifera* L., *Eugenia caryophyllata* thunb., *Vigna unguiculate* L., *Curcuma longa* L., *Camellia sinesis* L., and *Mucuna pruriens* L. were mixed in a ratio of 1:2:2:2:10:0.1:2:1:0.7:2, respectively.

Pre-Clinical Studies of Dietary Health Supplement in Rat Model of Parkinson's Disease The development of PD does not occur naturally in animals, except in humans. Therefore, different models are used to induce PD symptoms in animals, such as 6-hydroxydopamine (6-OHDA), 1-methyl-4-phenyl-1,2,3,6-tetrahydropyridine (MPTP), or rotenone are used to induce nigrostriatal dopaminergic lesions. In the current study, we have used rotenone-based in vivo assay for PD as it is the most relevant model among the available assays.

Rotenone is naturally occurring plant flavonoid, and a well-known neurotoxic pesticide that readily cross the blood-brain barrier due to its high lipophilic nature. It inhibits the mitochondrial complex-I of the electron transport chain (ETC), followed by ROS production. Nearly, all hallmarks of PD are replicated in rotenone induced animal model. It can be administered via intravenous (IV), intraperitoneal (IP), or oral route.

We developed the rotenone induced model, in which rats were injected with 2 mg/kg rotenone subcutaneously (s.c.) for consecutive 28 days. The rats were daily observed for various PD symptoms, such as piloerection, decrease mobility, tremors, and many others. Based on the observations of symptoms, rats were scored between 2-10, where 2 refers to lowest and 10 is highest PD score, as previously reported by Chen Xin and his colleagues (17-19). Following is the details scoring system that was used in PD model.

Scoring Criteria for Study Design II:
[21] Score 2: apart from the above indications, active mobility was reduced more obviously, and was accompanied with tremor, slow motion, and gait instability.
[22] Score 4: apart from the above indications, gait instability worsened, and the rats could not walk straight, rotating towards one side.
[23] Score 6: apart from the above performance, they lay obliquely towards one side or showed unilateral forelimb or hindlimb paralysis, and difficulty in walking and eating.
[24] Score 8: complete unilateral limb (forelimb or hindlimb) paralysis, limb spasms, rapid weight loss, and inability to eat.
[25] Score 10: agonal stage or death PD Model of Male Wistar Rats: In vivo rat PD model was developed, and the pre-clinical trials were conducted after the approval of the ICCBS ethical committee (ASP #2018-0007). 3 Months old, male Wistar rats (217 rats) were randomly divided into four groups, including control, pathological, standard drug, and supplement treated groups. The control group (10 rats) were s.c. injected with vehicle (myglyol 98%, DMSO 2%) only, and were used as reference. The remaining 210 rats were injected with rotenone (2 mg/kg) (dissolved in myglyol 98%, DMSO 2%) for 7-28 consecutive days depending on the appearance of PD symptoms. The animals were analyzed individually on daily basis and were scored accordingly. Among 210 rats, various PD symptoms were observed in 117 rats, while the remaining 93 rats did not show any signs or symptoms of PD. Therefore, 117 rats were further divided into pathological group (35 rats), standard drug treated (30 rats), and supplement treated (49 rats).

Pathological Group: The pathological/disease group included rats with score 2, 4, 6, and 8. These animals were left untreated after their respective scores, and were observed for the self-reversal of Parkinson's disease symptoms including motor (tremors, gait instability, decrease mobility, complete hind limb or fore limb paralysis), and non-motor symptoms (bad furs, piloerection, inability to eat, loss of body weight).

Among 35 pathological control rats, score 8 was observed in 10 rats, score 6 was observed in 7 rats, score 4 was observed in 8 rats, and score 2 was observed in 10 rats. The score 8 animals became completely paralyzed, and were not able to eat or drink independently so they were given the food and water using oral gavage.

Among score 8, only two rats (20% rats) showed self-reversal in PD symptoms, and move to score 4, and 6. However, conditions of remaining rats of score 8 (80% rats) became worsen and they moved to score 10 (death).

Among score 6 animals, two rats (28.5%) showed minor self-reversal in PD symptoms and move to score 4, while condition of one rat (14.2%) became worsen and moved to score 10 (death). However, remaining four rats (57.1%) were consistent at their developed PD score.

Among score 4 animals, four rats (50%) showed a minor self-reversal in PD symptoms and moved to score 2, while remaining four rats (50%) were remain consistent at their developed PD score. Among score 2 animals, all ten rats (100%) were consistent at their developed PD score.

Standard Drug Treated Group: Total 30 rats with scores 4, 6, and 8 were selected for the treatment with standard drug (Sinemet, a mixture of Carbidopa/Levodopa), which is the most successful drug approved by the U.S. Food and Drug Administration (FDA) for the treatment of symptoms associated with Parkinson's disease. According to the literature survey, patients can take up to the 5 tablets, depending upon the severity of the symptoms (20). The treatment dose is calculated using the Human Equivalent Dose of Parkinson Patients. Among 30 rats, score 8 was observed in 13 rats, score 6 was observed in 8 rats, and score 4 was observed in 9 rats.

Rats of score 8 were given 51 mg Sinemet/kg body weight. Among score 8 rats, only three (23% rats) showed improvement in PD symptoms and moved to score 6. However, conditions of remaining rats of score 8 (77% rats) became worsen, as they moved to score 10 (death).

Rats of score 6 were given 41 mg Sinemet/kg body weight. Among them, four rats (50%) showed improvement in PD symptoms, and move to score 4 and 2. However, two rats (25%) were consistent at their PD score and did not show any improvement in their conditions. Conditions of remaining two rats (25% rats) became worsen, and they moved to score 10 (death).

Rats of score 4 were given 31 mg Sinemet/kg body weight. Among them, only two rats (22%) showed improvement in PD symptoms and they move to score 2. However, conditions of one rat (11%) became worsen and moved to score 10 (death). Remaining five rats (55%) were consistent at their PD score and did not show any improvement in their conditions.

Supplement Treated Group: A total of 49 rats with scores 2, 4, 6, and 8 were selected for the treatment with supplement. Among 49 rats, score 8 was observed in 16 rats, score 6 was observed in 9 rats, score 4 was observed in 14 rats, and score 2 was observed in 10 rats.

Rats of score 8 were given supplement 2,000 mg/kg body weight. Among score 8, 6 rats (37.5% rats) showed improvement in PD symptoms and move to scores 4, and 2. However, conditions of remaining 10 rats (62.5% rats) became worsen and they moved to score 10 (death). These results were significant, in comparison to the standard drug treated group as the improvement was seen in only 23% rats.

Rats of score 6 were given supplement at a dose of 1,000 mg/kg body weight. All rats (100%) showed improvement in PD symptoms, and move to score 2.

Rats of score 4 were given supplement 600 mg/kg body weight. Among them, 13 rats (92.8%) showed improvement in PD symptoms, and move to score 2. Remaining one rat (7.2%) was consistent at its PD score, and did not show any improvement in its conditions.

Rats of score 2 were given supplement at a dose of 600 mg/kg body weight. Rats in this group showed improvement in various symptoms of score 2. For instance, their mobility was restored to normal, gait instability was decreased; and furs became white (back to normal). Only tremors and piloerection were not treated, so they were still considered at score 2.

In conclusion, rats in the group treated with dietary health supplement showed significantly improved behaviors, and had lower PD scores as compared to the pathological and drug treated groups. Whereas no improvement in PD symptoms was observed in 77% rats of pathological group indicating that the rotenone induced symptoms were not significantly reversed.

Acute and Chronic Toxicity of Testing Dietary Health Supplement: The pre-clinical toxicological studies of dietary health supplement have been carried out to determine the safety profile of this novel dietary formulation. The protocol based on OECD guidelines (20, 21) were used to study acute and chronic toxicity studies of dietary health supplement.

Protocol for The Acute and Chronic Toxicity Studies: Animals were divided into three groups with 10 animals per sex in each group. Group I served as blank, and was left untreated. Group II animals were given a single dose of 2,000 mg/kg dietary health supplement through oral gavage. Group III animals were given a single dose of 5,000 mg/kg dietary health supplement through oral gavage. Rats were carefully observed for the development of any toxic signs or symptoms for first 30 mins, and periodically (i.e. 60, 120, 240, and 360 mins, and then after 24 hours), and thereafter daily for consecutive 14 days.

Physical observation of animals included changes in skin colour (fur), lacrimation (red tears due to pain), salivation, piloerection (bristling or erection of hairs), frequent urination, tremors, convulsions, drowsiness, body weight, food consumption, and water consumption. The death of animals was also observed as mortality rate. After the completion of physical observation for 14 days', animals were dissected for the biochemical, and pathological studies.

Biochemical parameters of animals including blood glucose, creatinine, urea, liver function test, lipid profile, and complete blood count (CBC) were also analysed. Pathological studies of animals included the gross anatomical examination of vital organs including heart, liver, spleen, lungs, stomach, and kidneys.

For chronic toxicity, animals were divided into four groups with 10 animals each per sex in each group. Group I served as blank and was untreated. Group II, III, and IV animals were given doses of 925, 1850, and 3,700 mg/kg dietary health supplement through oral gavage consecutively for 3 months. As the supplement was found to be non-toxic in acute toxicity studies, so this time the rats were observed on daily basis for the physical symptoms (mentioned above), while the body weights were recorded weekly. After 3 months, the rats were dissected for biochemical tests, and gross pathology studies.

Results of Acute Toxicity: The animals were physically observed for various parameters. No change in skin or fur colour was observed, before and after the administration of dietary health supplement till 14 days. Lacrimation i.e., the secretion of tears from the eyes of rats, was not observed. Usually when rats are stressed or ill their eyes become red due to release of a red pigment called porphyrin. Urination was also found to be normal, indicating that the dietary health supplement is not inducing any kind of inflammation neither is affecting the kidneys. Salivation was also found to be normal. The food and water consumption in rats after the administration of dietary health supplement was also found to be normal.

There were no toxic signs and no mortality was observed after 14 days of administration of dietary health supplement. The animals were sacrificed, and the samples were analysed for biochemical tests, such as blood glucose, liver function test, CBC, and lipid profile. All biochemical parameters after the administration of dietary health supplement were found to be within the normal range indicating that the dietary supplement was not toxic for the rats upto a dose of 5,000 mg/kg. Based on the above-mentioned results it has been concluded that the dietary health supplement at the dose of 5,000 mg/kg is found to be safe during the acute toxicity studies. There was no significant change in the body weight, food, and water consumption was observed.

Heart, liver, spleen, kidneys, stomach, and lungs of rats from all groups were preserved in formalin for gross necropsy. The absolute and relative weights of organs after the administration of dietary health supplement were observed. There was no change in the relative and absolute weight of every organ in the animals, indicating that the supplement is safe to be used at a dose of 5,000 mg/kg. Furthermore, no mortality was observed till 14 days after administration of dietary health supplement.

Results of Chronic Toxicity: Three different doses of dietary health supplement i.e. 925, 1850, and 3,700 mg/kg body weight (representing half of the Human Equivalent dose, the Human Equivalent dose, and double the Human Equivalent dose, respectively, were given to Albino Wistar rats (male and female) for 3 months. In chronic toxicity testing, all animals were observed daily for the development of any toxic signs or symptoms for 3 months.

Biochemical tests, such as blood glucose, liver function test, CBC, and lipid profile were also carried out. All the biochemical parameters after the administration of dietary health supplement were found to be within the normal range, indicating that the dietary supplement was not toxic for the rats up to the dose of 3,700 mg/kg. Based on the above-mentioned results it has been concluded that the dietary health supplement up to the dose of 3,700 mg/kg was safe to animals during the chronic toxicity studies.

Brain, liver, and kidneys were preserved in formalin for histopathology studies. The absolute and relative weights of different organs after the administration of dietary health supplement were observed. There was no change in the relative and absolute weight of every organ in the animals, indicating that the supplement is safe to be used upto a dose of 3,700 mg/kg.

What is claimed is:

1. A method of reducing the symptoms of Parkinson's disease in humans comprising administering to as subject in need thereof a dose of 600 mg/kg to 1000 mg/kg of an aqueous mixture of one-part *Allium sativum* L. (as fresh juice of rhizomes), two parts *Prunus dulcis* (Mill.) D. A. Webb. (as dry fruit powder), two parts *Arachis hypogaea* L. (as dry fruit powder), two parts *Solanum lycopersicum* L. (as fruit dried under shade and then powdered), ten parts *Vitis vinifera* L. (as fresh juice), 0.1 parts *Eugenia caryophyllata* Thunb. (as seed oil), two parts *Vigna unguiculata* L. (as dried seed powder), one-part *Curcuma longa* L. (as rhizome powder), 0.72 parts *Camellia sinensis* L (as leaf extract), and two parts *Mucuna pururiens* L. (as roasted seed powder).

2. The method of claim 1, wherein the said composition further contains suitable inactive pharmaceutical ingredients.

* * * * *